United States Patent
Curatolo et al.

Patent Number: 5,443,843
Date of Patent: Aug. 22, 1995

[54] GASTRIC RETENTION SYSTEM FOR CONTROLLED DRUG RELEASE

[75] Inventors: William J. Curatolo, Niantic; Jeelin Lo, Old Lyme, both of Conn.

[73] Assignee: Pfizer Inc., New York, N.Y.

[21] Appl. No.: 632,877

[22] Filed: Dec. 24, 1990

Related U.S. Application Data

[62] Division of Ser. No. 200,801, May 31, 1988, Pat. No. 5,002,772.

[51] Int. Cl.⁶ .................................................. A61K 9/20
[52] U.S. Cl. ..................... 424/464; 424/438; 424/469
[58] Field of Search ............. 604/892.1; 424/438, 424/464, 469

[56] References Cited

U.S. PATENT DOCUMENTS

| | | | |
|---|---|---|---|
| 3,844,285 | 10/1974 | Laby | 128/260 |
| 4,251,506 | 2/1981 | Laby | 424/438 |
| 4,312,347 | 1/1982 | Magoon et al. | 128/260 |
| 4,601,893 | 7/1986 | Cardinal | 424/15 |
| 4,687,480 | 8/1987 | Laby | 424/438 |
| 5,002,772 | 3/1991 | Curatolo et al. | 424/438 |

FOREIGN PATENT DOCUMENTS

| | | |
|---|---|---|
| 514312 | 6/1977 | Australia. |
| 079724 | 5/1983 | European Pat. Off. . |
| 202159 | 11/1986 | European Pat. Off. . |

Primary Examiner—Golladmudi S. Kishore
Assistant Examiner—William E. Benston, Jr.
Attorney, Agent, or Firm—Peter C. Richardson; Paul H. Ginsburg; Grover F. Fuller, Jr.

[57] ABSTRACT

An oral drug delivery system having delayed gastrointestinal transit comprising a non-continuous compressible element and an attached controlled release device and which in the expanded form resists gastrointestinal transit; and a modular system for use therein comprising a non-continuous compressible element and an attached receptacle means for receiving and holding a drug-containing orally administrable controlled release device and which in the expanded form resists gastric transit.

8 Claims, 1 Drawing Sheet

GASTRIC RETENTION SYSTEM FOR CONTROLLED DRUG RELEASE

This is a division of application Ser. No. 07/200,801, filed on May 31, 1988, now U.S. Pat. No. 5,002,772.

BACKGROUND OF THE INVENTION

1. Field of the Invention

This invention relates to an oral drug delivery system having delayed gastrointestinal transit. More specifically it relates to a gastric retention system for controlled release of drugs to the gastrointestinal tract. The system comprises one or more non-continuous compressible elements, i.e., retention arms, and an attached controlled release device and which in the expanded form resists gastrointestinal transit. It further relates to a modular system for use therein comprising one or more non-continuous compressible elements and an attached receptacle means for receiving and holding a drug-containing orally administrable controlled release device and which in the expanded form resists gastrointestinal transit.

2. Description of the Prior Art

Means for achieving retention of drugs in the gastrointestinal tract and for controlled release of said drugs therein ahs been a long sought objective. Upon per os administration of a drug or drug preparation most, if not all of it, usually passes from the stomach to the small intestine in a relatively short time, generally on the order of one to two hours. This behavior necessitates frequent per os administration of a drug, the beneficial effect of which is to be exhibited in the stomach or the wall thereof. For some drugs, efficient absorption occurs only in the upper gastrointestinal tract, i.e., the stomach and/or the small intestine. Slow release formulations of such drugs may only be effective for a short time period, generally 4–5 hours, because the formulation passes into the colon, where drug absorption may be inefficient or nonexistent. In such cases, retention of a controlled release drug preparation in the upper gastrointestinal tract would be advantageous.

Retention of drugs or drug formulations in the proximal region of the gastrointestinal tract in order for said drug or formulation to achieve its beneficial effect poses a difficult problem. Davis et al., Int. J. Pharm. 21, 331–340 (1984) teach that gastrointestinal transit of a pharmaceutical dosage form depends upon several factors such as size, shape and nature of the system; i.e., whether single unit or multiparticulate; and upon physiological factors, especially upon the presence or absence of food in the stomach. The stomach is known to empty different materials at different rates and to break down digestible materials to about 2 mm or less before they pass through the pylorus into the duodenum. Meals of high calorific value and certain foodstuffs, especially fats, appear to have an inhibitor effect on gastric emptying [Davis et al., Int. J. Pharm. 21, 167–177, (1984)].

Retention of indigestible materials in an empty stomach is further complicated by the ability of the gastrointestinal tract to undergo powerful contractions called the interdigestive myoelectric complex (IMC), also known as interdigestive migrating motor complex, or more simply, "housekeeper wave". This phenomenon tends to sweep indigestible materials from an empty stomach past the pylorus into the duodenum and through the remainder of the small intestine.

Various methods have been described in the literature in efforts to achieve retention and controlled release of drugs in the gastrointestinal tract.

U.S. Pat. No. 3,976,764, issued Aug. 24, 1976, describes hollow globular shells having an undercoating of a cellulose acetate-phthalate copolymer and an outer coating of ethyl and hydroxypropyl celluloses in combination with a pharmaceutically active ingredient. Said coated globular shells are reported to float in the gastric juices when taken internally to provide prolonged release of the active ingredient. Other flotation devices are described in U.S. Pat. Nos. 4,140,755 and 4,167,558.

EP Application 0168862, published Jan. 22, 1986, describes biodegradable hollow fibers containing an active substance in their cavities for controlled release of said substance when implanted subcutaneously in mammals. U.S. patent application Ser. No. 38,189, filed Apr. 14, 1987 describes drug-containing fibers having an axial ratio of at least about 8 which are useful for retention in the gastrointestinal tract.

Mitra, Polymer Preprints, ACS Div. Polymer Chemistry, 24 (1), 51–52 (1983), and U.S. Pat. No. 4,451,260, issued May 29, 1984, describes an oral sustained release drug delivery system, a laminate, comprising a carrier film containing drug in a matrix and a barrier film on one or both surfaces of the carrier film. The barrier film serves to control the rate of release of the drug and also provides buoyancy to the delivery system by virtue of air bubbles between it and the carrier film. The composite is generally cut into long narrow strips $2.1 \times 14$ cm$^2$, optionally pleated before being packed into gelatin capsules.

EP 202159, published Nov. 20, 1986, describes gastric retention devices comprising a continuous solid-stick figure, a planar figure or ring figure made from polymers. A drug may be dispersed within the device as an integral part thereof, or may be attached as a controlled release drug module to the aforementioned retention devices.

Orally administrable devices of variable geometry; i.e., devices which have one configuration designed to permit their oral administration and which, when in the environment of use, assume a second configuration designed to prevent their expulsion are known in the literature. Principle focus upon such devices has occurred in animal husbandry and particularly in the treatment of ruminants. Representative of such devices are those disclosed in U.S. Pat. No. 3,844,285 and 4,601,893.

In spite of the developments in gastric retention devices the need for practical means for achieving retention of drugs or drug formulations in the stomach for controlled (sustained, predictable and reproducible) release of drugs regardless of whether the stomach is full, empty or anywhere in between is highly desirable. Especially desirable is such a system which can be applied to existing orally administrable controlled release devices to enhance their gastric retention so as to render them essentially independent of the condition of the stomach.

SUMMARY OF THE INVENTION

This invention relates to an oral drug delivery system for human or animal use. The system, a gastric retention system, exhibits delayed gastrointestinal transit. It comprises one or more retention arms, said arms being a non-continuous compressible element, and an attached controlled release device and which in the expanded form resists gastric transit; and to a modular system for use therein comprising a non-continuous compressible element and an attached receptacle means for receiving and holding a drug-containing orally administrable controlled release device and which in the expanded form resists gastric transit. It especially relates to such systems to which are attached two or more flexible retention arms. More specifically it relates to such systems wherein the non-continuous elements, e.g. retention arms, are compressible about the device or the receptacle means to an overall size suitable for oral administration thereof and which, in a liquid use environment, are expandable to an overall size sufficient to prevent passage thereof through a pylorus, said receptacle means and/or said non-continuous elements being erodible in the use environment.

BRIEF DESCRIPTION OF THE DRAWING

FIG. I shows a partially uncoiled system of this invention (1) comprising a receptacle (2) to which are attached four retention arms (3) and having a controlled release tablet (4) in the receptacle.

DETAILED DESCRIPTION OF THE INVENTION

Figure 1:
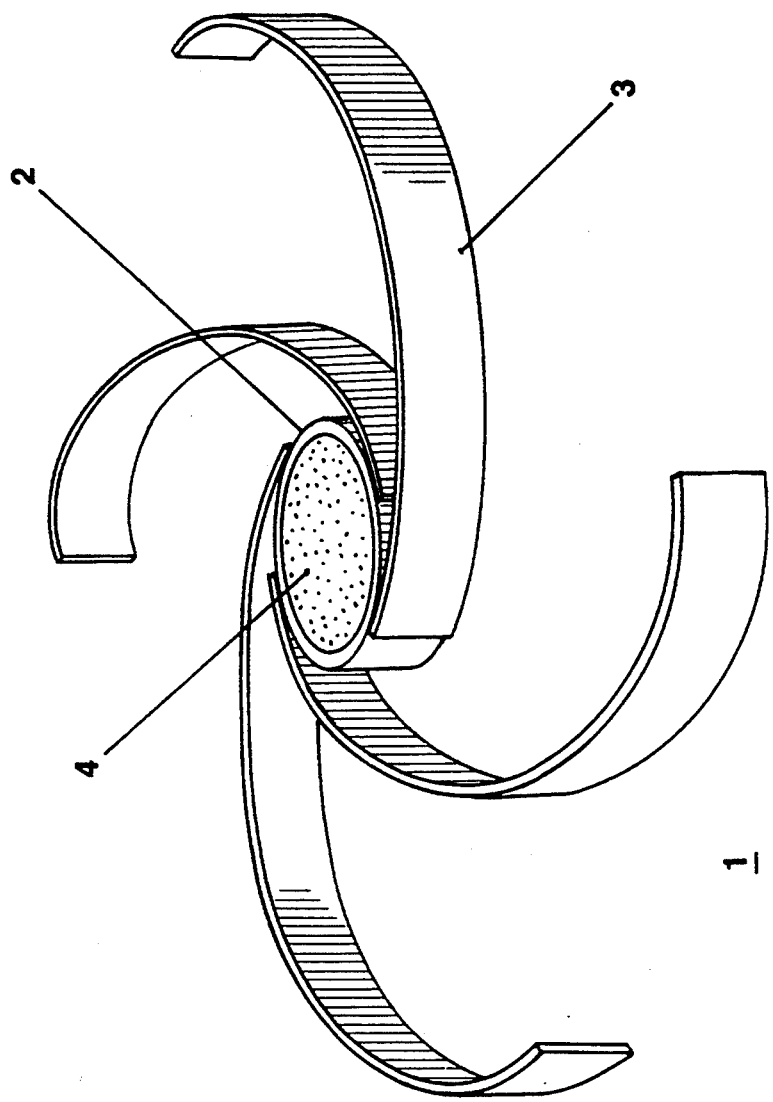

The term "orally administrable controlled release device" as used herein is intended to refer to tablets and capsules generally described as prolonged, controlled, delayed or sustained release devices designed for oral administration. The mechanism by which such devices operate is immaterial to the present invention. Such devices per se form no part of this invention. The controlled release devices can, on the basis of their construction, be referred to as matrix, laminate (or sandwich), coated matrix, reservoir or osmotic devices. Alternatively, from the standpoint of their mechanism of action they can be characterized as diffusion or osmotic devices. The matrix type includes tablets having the drug dissolved or suspended in them, and laminated devices such as those wherein the drug-containing carrier is sandwiched or interposed between non-drug containing layers of a carrier. The reservoir devices comprise a drug supply or drug plus excipient core surrounded by a wall formed by a polymeric or wax carrier.

Representative of an osmotic device is one which comprises a water-insoluble, water permeable polymer, optionally comprising a porosigen dispersed therein and containing within the reservoir an osmotic enhancing agent and drug supply.

Representative of such devices are those described in U.S. Pat. Nos. 4,687,660; 4,572,833; 4,552,625; 4,454,108; 4,434,153; 4,389,393; 4,327,725; 3,845,770; 3,835,221; 2,887,438; EP 169,105 and EP 162,492.

As used herein, the term "controlled release" is intended to embrace not only the concept of sustained release of drug over a prolonged period of time; i.e., relative to the time period the drug response is realized by administration of a single dose of the drug; but those of predictability and reproducibility. Thus, this invention permits both rate-wise and time-wise release of drug; i.e., drug is released at a fixed, reproducible rate over a predetermined period of time. In the present instance, the herein described gastric retention system extends the term to include drug release primarily at a pre-determined site; namely, the proximal region of the gastrointestinal tract.

The terms "receptacle" and "receptacle means" refer to any means for receiving and holding a controlled release tablet or controlled release capsule. It can, by definition, have any of a variety of configurations and dimensions depending upon the size and shape of the device (tablet or capsule) to be used. For convenient use for oral administration of drugs, its maximum size is, of course, limited by the host to be treated; e.g. humans or animals. Again, for convenience and ease of administration, it should have no sharp or projecting features and is desirably round, circular or elliptical.

The receptacle can, in one modification of this invention, be in the form of a collar or a belt which fits about, i.e. contains, a given controlled release device so as to hold it until such time as it is to be expelled from the host to whom it was administered.

In another modification, the receptacle means is an open-ended container, i.e., a cup-shaped container; the overall configuration and dimensions of which are determined by those of the controlled release device it is to contain.

In those instances wherein the receptacle is a collar or an open-ended container, it can be constructed from a solid impermeable polymer since in many situations there will be sufficient exposure of the controlled release device to the liquid of the environment.

In a further modification, the receptacle means can be a closed container; i.e. one having a top, a bottom and sides, which completely enclose the controlled release device, having substantially the same configuration but somewhat larger dimensions to accommodate the device. For such modification the receptacle is generally constructed of a polymer which is permeable, including microporous, as discussed below with respect to the retention arms. Alternatively, it can be constructed from an impermeable or semipermeable polymer in which macroperforations have been made to permit passage of environmental liquid into the receptacle and passage of environmental liquid plus drug into the environment.

The term "drug" as used herein includes physiologically or pharmacologically active substances which produce a systemic or localized effect or effects in a mammal, including humans and animals. Included in this term are sedatives such as phenobarbital, thiopental and sodium pentobarbital; analgesics such as codeine, morphine and mependine; levo-dopa; tranquilizers such as reserpine, chlorpromazine and fluphenazine; antibacterials such as tetracycline, oxytetracycline, penicillin, sulfonamides and chloramphenicol; antifungals such as tioconazole, griseofulvin and nystatin; antiinflammatories such as aspirin and salicylamide; nutritional agents such as essential amino acids, vitamins C and $B_{12}$; bronchodilators such as pirbuterol; diuretics such as furosemide; antihypertensives such as prazosin and doxazosin; vasodilators such as nifedipine; prostaglandins, anthelmintics, antiulcer agents; and others known to those skilled in the art.

The amount of a given drug which must be used in a delivery system of this invention to achieve a given release rate, or the release rate of a given system of this invention, is determined by an in vitro test as those skilled in the art will recognize. In general, such a test involves placing one or more of the systems in question in an environment approximating the ambient environment of ultimate use intended for said drug delivery system and measuring by appropriate methodology known to those skilled in the art the amount of drug released to said environment over a given period of time and/or by determining the amount of drug remaining in the system after a given period of time.

As regards solubility of a given drug, there is no upper limit since the release rate can be regulated by judicious choice of polymer or polymers. As regards a lower limit of solubility, the drug should be of sufficient solubility to permit achievement of a beneficial dose of the drug from the maximum number of systems which can be practically administered to a given subject.

The term "retention arm" refers to any ribbon, ribbon-like, fiber, or fiber-like structure in which one dimension, e.g., length, is significantly greater than the other dimensions, e.g., width, thickness, or diameter. Said aforementioned structures can be solid or hollow and, if hollow, can be closed at the end or ends. The retention arms can themselves serve as controlled release devices for the same or different drug from that of the controlled release device (tablet or capsule). Thus, the opportunity for concurrent controlled release of more than one drug in a convenient and simple manner is made available.

As regards the present invention, it is generally preferred to use retention arms which are not themselves controlled release devices since such systems are simpler to construct.

The retention arms can comprise a material which is bioerodible and, especially when the retention arms are to serve as a controlled release device, it can be permeable, including microporous, semipermeable or impermeable. By permeable retention arm is meant one comprising a polymer, which allows passage of environmental fluid and of drug. A semi-permeable retention arm, on the other hand, is one which is permeable to environmental fluid and essentially impermeable to the drug or vice-versa. An impermeable retention arm is one comprising material essentially impermeable to environmental fluid and drug. The selected material can, in addition, be non-erodible or bioerodible in the use environment.

The retention arm material which is used must be non-toxic to the mammal, including a human, to which the drug delivery system is to be administered, and sufficiently flexible to permit ease of administration and to avoid infliction of puncture wounds during and subsequent to administration. Representative of the polymeric materials which can be used are polyethylene, polypropylene, polystyrene, polytetrafluoroethylene, polyvinyl chloride, cellulose acetate, cellulose nitrate, cellulose triacetate, ethylene vinylacetate, polyesters, polyanhydrides, polyorthoesters, hydroxylated-ethylene vinylacetate, hydroxyethyl cellulose, acetylated hydroxyethyl cellulose, fibroin, polyglycolic acid, polylactic acid, poly(lacticglycolic)acid, cellulose acetate succinate, cellulose ethers, poly(vinylmethyl ether) copolymers, cellulose acetate laurate, polyacrylates, organosilicon polymers, methyl cellulose, polyether and polyester urethanes, polyacrylonitrile, polysulfide elastomer, polyisoprene, poly (vinylpyrrolidone), polyamides, polyimides, polyamides and methacrylates. Still further, the "arm" can be constructed of a metal or metal alloy. A polymeric system of interest comprises a polymer which is "enteric"; i.e., a polymer which is insoluble at gastric pH and soluble at intestinal pH (e.g. cellulose acetate-phthalate).

The entire oral drug delivery system or only a portion thereof can be made from polymers which lose strength via erosion by dissolution, hydrolysis or enzymatic degradation. These polymers include: polyethylene glycol, polyethylene oxide, polyacrylic acid, polyvinyl alcohol, dextran, gelatin, polyvinyl pyrrolidone, hydroxypropylmethylcellulose, cellulose acetate phthalate, hydroxypropylcellulose, hydroxypropylmethylcellulose phthalate, polyvinylacetate phthalate, polyacrylamide, polysaccharides, gum arabic, Eudragit E100 (copolymer of dimethylaminoethyl methacrylate and methacrylic acid ester), Eudragit L100 (copolymer of methacrylic acid and methacrylic acid ester), polyorthoesters, polyphosphates, glutamic acid and ethyl glutamate copolymer, polyglycolic acid, polylactic acid, copolymer of lactide and $\epsilon$-caprolactone, terpolymer of lactide, glycolide and $\epsilon$-caprolactone.

Non-polymeric additives which dissolve upon hydration to decrease the strength of the stiff component of the device include: organic substances such as citric acid, glucose and the like; and inorganic salts such as sodium bicarbonate, sodium chloride and the like.

Part of the device can also be made from polymers which lose strength upon hydration. These polymers include crosslinked hydrogels such as polyhydroxyethylmethacrylate and the like.

Methods to combine materials to give the desired properties are known to those skilled in the art and include blending, laminating, casting, coextrusion, injection molding and compression molding of polymers; adding organic substances, inorganic salts or rubber particles to a polymer, with or without coupling agents such as organic titanates and silanes; crosslinking of two polymers with hydrolyzable bonds; and copolymerization.

The retention arms can be attached directly to the controlled release device by appropriate means such as by gluing or by fusing them to said device. This latter method is particularly convenient when the device and retention arms are constructed from the same polymer. The fusion can be accomplished by thermal means for certain polymers e.g. polyethylene; or by means of a suitable solvent. In either instance, the retention arms and device become an integrated unit. Alternatively, the receptacle and retention arms may be constructed as a single piece from a material which possesses the requisite properties to support gastric retention and to insure eventual loss of physical integrity in order to assure safe passage out of the stomach. It may in certain situations be difficult to conclude how many retention arms are attached to a given device. In order to avoid semantic problems on this issue it is intended, for purposes of this invention, that when any retention arms extends beyond a given edge of the controlled release device it is considered a separate retention arm.

The retention arms (or simply, arms) must be flexible enough to prevent puncture of the stomach or intestinal wall and to permit their being wrapped or otherwise compressed about the device or receptacle means for administration purposes. The desired flexibility is related to the length of the arm used. Long arms require a greater degree of flexibility than do short arms. They must also possess the ability, in the use environment, of expanding from their compressed state to, or approximately to, their configuration prior to their being compressed. The suitability of a particular arm length is determined by empirical determination of gastrointestinal transit time assayed, for example, by X-ray radiography or scintigraphy. The flexibility of materials used in constructing retention arms found acceptable by either of these methods is then measured, if desired, by the American National Standard ANSI/ASTM Standard Test Method for Stiffness of Fabrics, D1388-64, Option B Double Cantilever Test.

The above described X-ray radiography or scintigraphy methods are also used to determine the retention time of a given system in the host to which it is administered.

The overall dimensions of the orally administrable systems of this invention are determined by the anatomy and physiology of the mammal to which they are to be administered. In the unused condition they must be of a size suitable for oral administration to the mammal to be treated. For human use, from a practical standpoint, the largest dimension of the systems in the expanded condition can vary from 2.5 to 6.0 cm, and preferably from 3.0 to 5.0 cm. The herein described systems can have a variety of configurations determined in part by that of the controlled release device used. When the system is other than round or circular, the minimum and maximum dimensions are 2.5 and 6.0 cm, respectively for the expanded form.

The major factors responsible for retaining the herein described delivery systems in the gastrointestinal tract are their overal dimensions (length and width), their configuration and the stiffness of the arms. Thus, for systems having arms of identical dimensions but different stiffness, the least flexible will be retained for a longer period of time.

The preferred configuration for the oral drug delivery systems of this invention is that of a coil or spiral. In those systems in which a single arm is present, the controlled release device, or the module, is located at the center of the coil; i.e., the retention arm is coiled around the said device or module. As a matter of fact, in the preferred configuration of all oral drug delivery systems of this invention, the controlled release device or module is located at the center of the coil.

Various embodiments of the current invention are possible. A preferred embodiment of this invention is one in which a single retention arm is attached to and coiled about the controlled release tablet or capsule, either directly or via a receptacle, and in which the retention arm uncoils at least partially in the environment of use, to form a coil or coil-like configuration around the controlled release device. In this embodiment, the retention arm may possess a fiber-like or a ribbon-like shape. The preferred retention arm length for this embodiment depends upon the stiffness of the material from which the retention arm is constructed; for a stiffer material, a shorter length may be required. In the uncoiled state, the diameter of the coil formed by the retention arm is preferably greater than approximately 3 cm. The length of the retention arm in this embodiment is typically 10–30 cm.

A more preferred embodiment is one in which two or more, most preferably four, retention arms are attached to and coiled about the controlled release tablet or capsule, either directly or preferably via a receptacle, and in which the retention arms uncoil at least partially in the environment of use. In this most preferred embodiment, the retention arms preferably possess a ribbon-like shape. The preferred retention arm length for this embodiment depends upon the stiffness of teh material from which the retention arm is constructed; for a stiffer material, a shorter length may be required. In the uncoiled state in the environment of use, the diameter of the gastric retention system is preferably greater than approximately 3 cm. The length of the retention arms in such embodiment is typically 2–6 cm.

In all preferred embodiments, the receptacle and/or the retention arms, and/or the adhesive which attaches the retention arms to the receptacle or directly to the drug delivery device, are constructed from materials which soften, disintegrate, dissolve or degrade in the biological environment of use, in order to permit safe timely exit from the stomach and safe passage through the distal GI tract, with no danger of intestinal obstruction.

A procedure of value in determining the release rates of the herein described drug containing device is as follows. The procedure, an in vitro procedure, comprises placing the device or devices in an environment approximating that of the gastrointestinal tract and measuring the amount of drug released to said environment as a function of time.

In vivo release of drug from oral drug delivery systems of this invention is determined by administering them to dogs and measuring the amount of drug released over a period of time by determining the amount of drug present in, for example, the animals' blood or urine.

In the Examples which follow, the retention arms, are preferably symmetrically placed about the controlled release device or the receptacle means containing such a device since, for a given system wherein all retention arms are substantially of equal flexibility and overall dimensions, they are retained for longer periods than those systems having non-symmetrical arrangement of retention arms.

The following Examples are illustrative, but not limiting of the present invention.

In each Example, the dogs were concurrently dosed with the oral delivery system and with a radiopaque non-disintegrating $BaSO_4$ tablet to serve as internal control. Dogs were fed at 7 hours post-dose.

Abbreviations used in the tables are:
I/I=control tablet in stomach/delivery system in stomach; O/I=tablet out/delivery system in; O/O=tablet out/delivery system out; NM=not measured.
diam=diameter.

EXAMPLE 1

Gastric retention of fibers in unfed beagle dogs was assessed using x-ray radiography. Hollow polyethylene fibers (10 cm length × 1 mm outer diameter) were filled with a saturated solution of potassium iodide, which served as a radiopaque agent. The ends were tied and the fiber was coiled and placed in a #00 gelatin capsule. The gelatin capsule also contained a 4.0 mm × 1.5 mm radiopaque non-disintegrating standard round convex tablet of barium sulfate, which served as an internal control for GI transit studies. Fasted beagle dogs were dosed with the capsule, which contained both the fiber and the tablet, and were x-rayed at various times after dosing in order to assess the positions of the fiber and tablet in the GI tract. The dogs were fed their normal daily food ration at ~7 hours post-dose. Table I demonstrates that the fiber was consistently retained longer than the tablet in the stomach. While the tablet was generally emptied from the stomach in 1–2 hours, the fiber was consistently gastrically retained for ≧24 hours. This gastric retention was particularly significant because it was observed in the unfed state, which is characterized by housekeeper waves which remove indigestible material from the stomach.

The gastric retention of tablets with attached retention arms of polyethylene fibers was similarly assessed in unfed dogs. A 0.4 cm×0.15 cm radiopaque non-disintegrating standard round convex tablet (BaSO4) was drilled through with a 0.11 mm hole through the center of the tablet face. A 10 cm×0.1 cm hollow polyethylene (PE) fiber was threaded into the hole in the tablet face in one of two configurations, and was glued to the tablet. In one configuration, the tablet was located at the end of the fiber retention arm; in the other configuration the tablet was located at the center of the fiber retention arm. These devices can be visualized as a tablet with a single 10 cm fiber retention arm attached, and as a tablet with two 5 cm fiber retention arms attached, respectively. The fiber retention arms were loaded with a small quantity of steel powder, as a radiopaque agent. Each device was loaded into a #00 capsule, along with a control radiopaque tablet. Table I presents the observed extent of gastric retention in unfed dogs of a 0.4 cm×0.15 cm tablet with a 10 cm PE fiber retention arm attached, and of a 0.4 cm×0.15 cm tablet with two 5 cm PE fiber retention arms attached. The tablet with a single 10 cm PE fiber retention arm was retained for only one hour longer than the control tablet in one dog, and was not retained at all in two other dogs. This result was surprising, since a 10 cm PE fiber alone was consistently gastrically retained for ≧24 hours (Table I). These observations demonstrate that attachment of a tablet to a fiber can result in a large decrease in the ability of the fiber to withstand "housekeeper waves" and be retained in the stomach. Thus, design of an effective gastric retention device for a tablet is not a trivial matter.

The behavior of tablets with two 5 cm fiber retention arms was significantly different. Table I demonstrates that, in two out of three unfed dogs, this device was gastrically retained significantly longer than a control tablet. In one case, the tablet/fiber device was retained for at least 24 hours. In one dog, both the device and the control tablet were retained for less than one hour. These data demonstrate that a tablet with two fiber retention arms can be gastrically retained for a significantly longer time than a control tablet. However, the duration of retention is variable.

TABLE I

Tablet With Attached Fiber Retention Arms — Effect of Number of Fibers and Fiber Length Gastric retention in unfed beagle dogs of (A) hollow polyethylene (PE) fiber (10 cm length × 1 mm outer diameter), (B) non-disintegrating tablet BASO4 (4.0 mm diameter × 1.5 mm thickness) with a single attached hollow PE fiber retention arm (10 cm × 1 mm), (C) non-disintegrating tablet (4.0 mm × 1.5 mm) with two attached hollow PE fiber retention arms (5 cm × 1 mm). In each case a radiopaque non-disintegrating control tablet (4.0 mm × 1.5 mm) was dosed along with the experimental device.

| | DEVICE | GASTRIC RETENTION AT VARIOUS TIMES (HOURS) POST-DOSE | | | | | | |
|---|---|---|---|---|---|---|---|---|
| | | 1 | 2 | 3 | 4 | 5 | 6 | 24 |
| (A) | 10 cm PE Fiber | | | | | | | |
| | Dog A | I/I | O/I | O/I | O/I | O/I | O/I | O/I |
| | Dog B | O/I | O/I | O/I | O/I | O/I | O/I | O/I |
| | Dog C | I/I | O/I | O/I | O/I | O/I | O/I | O/I |
| (B) | 0.4 cm Tablet with attached 10 cm PE FRA* | | | | | | | |
| | Dog A | I/I | I/I | O/I | O/O | NM | NM | NM |
| | Dog B | O/O | NM | NM | NM | NM | NM | NM |
| | Dog C | O/O | NM | NM | NM | NM | NM | NM |
| (C) | 0.4 cm Tablet with two attached 5 cm PE FRA | | | | | | | |
| | Dog A | O/I | O/I | O/I | O/O | NM | NM | NM |
| | Dog A | O/I | O/I | O/I | O/I | O/I | O/I | O/I |
| | Dog B | O/I | O/I | O/I | O/I | O/O | NM | NM |
| | Dog B | I/I | I/I | O/I | O/I | O/O | NM | NM |
| | Dog C | O/O | NM | NM | NM | NM | NM | NM |
| | Dog C | O/O | NM | NM | NM | NM | NM | NM |

*FRA = fiber retention arm(s).

EXAMPLE 2

The effects of tablet size on gastric retention of tablet/fiber devices was assessed in unfed beagle dogs. Radiopaque non-disintegrating tablets (0.64 cm diameter×0.32 cm thickness) were prepared with two attached hollow radiopaque PE fiber retention arms (5 cm length×0.1 cm diameter), as described above in Example 1 (FIG. 1B). These tablets were significantly larger than those reported in Example 1 (0.4 cm×0.15 cm). Table II presents the duration of gastric retention of these devices in unfed beagle dogs. In one dog, the device was gastrically retained for only one hour longer than a control tablet. In the other two dogs tested, the device was retained no longer than the control tablet. Gastric retention data for the 0.4 cm tablet with two attached 5 cm fiber retention arms are also included in Table II. It is clear that the device with the smaller tablet is better retained.

TABLE II

Tablet With Attached Fiber Retention Arms Effect of Tablet Size

Gastric retention in unfed beagle dogs of (A) non-disintegrating BASO4 tablet (0.64 cm diameter × 32 cm thickness) with two attached hollow PE fiber retention arms (5 cm length × 0.1 cm outer diameter); (B) non-disintegrating tablet (0.4 cm diameter × 0.15 cm thickness) with two attached hollow PE fiber retention arms (5 cm length × 0.1 cm outer diameter).

| | DEVICE | GASTRIC RETENTION AT VARIOUS TIMES (HOURS) POST-DOSE | | | | | | |
|---|---|---|---|---|---|---|---|---|
| | | 1 | 2 | 3 | 4 | 5 | 6 | 24 |
| (A) | 0.64 cm Tablet with two attached 5 cm PE FRA | | | | | | | |
| | Dog A | I/I | O/I | O/I | NM | NM | NM | NM |
| | Dog B | O/O | O/O | NM | NM | NM | NM | NM |
| | Dog C | I/I | I/I | I/I | I/I | O/O | O/O | NM |
| (B) | 0.4 cm Tablet with attached 5 cm PE FRA | | | | | | | |
| | Dog A | O/I | O/I | O/I | O/O | NM | NM | NM |
| | Dog A | O/I | O/I | O/I | O/I | O/I | O/I | O/I |
| | Dog B | O/I | O/I | O/I | O/I | O/O | NM | NM |
| | Dog B | I/I | I/I | O/I | O/I | O/O | NM | NM |
| | Dog C | O/O | NM | NM | NM | NM | NM | NM |
| | Dog C | O/O | NM | NM | NM | NM | NM | NM |

EXAMPLE 3

Gastric retention of a 0.4 cm×0.15 cm radiopaque non-disintegrating tablet (BaSO4) with two attached 5 cm×0.1 cm PE fiber retention arms (FIG. 1B) was assessed in fed dogs. Immediately after dosing, each dog was fed its normal daily ration of dry food and was allowed access to water. Table III presents gastric retention data for these devices in fed dogs, and also presents retention data in unfed dogs for comparison. The tablet/fiber device was consistently retained in fed dogs for >11 hours (the duration of the experiment). In two out of the three dogs, the non-disintegrating control tablet was also retained. These results are consistent with current understanding of the physiology of stomach emptying. Solid objects, e.g. pharmaceutical dosage forms, which are larger than ~0.2-0.5 cm are retained in the stomach in the fed state, while objects in this size range are quickly emptied (0-2 hours) by migrating motor complexes or "housekeeper waves" in the unfed state.

TABLE III

Retention in Fed Dogs

Gastric retention in fed beagle dogs of a non-disintegrating BASO$_4$ tablet (0.4 cm diameter × 0.15 cm thickness) with two attached hollow PE fiber retention arms (5 cm length × 0.1 cm outer diameter).
GASTRIC RETENTION AT VARIOUS TIMES (HOURS) POST-DOSE

| DOG | 1 | 2 | 3 | 4 | 5 | 11 |
|---|---|---|---|---|---|---|
| A | I/I | I/I | I/I | I/I | I/I | I/I |
| B | I/I | I/I | I/I | I/I | I/I | I/I |
| C | O/O | O/I | O/I | O/I | O/I | O/I |

EXAMPLE 4

The gastric retention of a tablet with an attached coil was assessed. A radiopaque non-disintegrating tablet (0.64 cm diameter × 0.32 cm thickness) was prepared and a 0.24 cm hole was drilled through the entire tablet at the center of the tablet face. A 20 cm piece of hollow PE fiber (20 cm length × 0.24 cm diameter) was wound into a coil with an ~3 cm diameter, and was held in this configuration with a piece of autoclave tape. The PE coil was placed in a 75° C. oven for 1 hour, to permit the PE to set in its coiled configuration. A 20 cm piece of nylon monofilament fiber (20 cm length × 0.13 cm diameter) was similarly coiled and taped, and was "set" in a 125° C. oven for 1 hour. The coiled nylon monofilament was thread into the coiled hollow PE fiber, stainless steel powder was poured into the void space between the nylon and PE to provide radiopacity, and the ends of the fiber were sealed with cyanoacrylate glue. The end of the fiber was thread into the tablet hole and glued. The final device consisted of an ~3.5 cm diameter coil, with a tablet attached to one end (via the tablet face). The fiber retention arm on the tablet/fiber coil device was compressed, and the device was placed in a #000 gelatin capsule. When a device of this type was placed in water or aqueous buffer at 37° C., the gelatin capsule dissolved within 5-15 minutes and the fiber retention arm uncoiled partially so that the overall diameter of the uncoiled tablet/fiber device was ~4 cm.

Table IV presents the duration of gastric retention of tablet/fiber coil devices in fasted beagle dogs who were fed their normal daily food ration at ~7 hours post-dose. In all cases, the tablet/fiber coil device was gastrically retained for >24 hours, while the control tablet was retained for <2 hours. This embodiment of the invention is a preferred one because (a) a >24 hours gastric retention is observed, and (b) a large controlled release tablet can be incorporated to deliver a high sustained dose exclusively in the stomach, thus improving bioavailability and eliminating the "window of absorption" problem.

TABLE IV

Fiber Coil with Attached Tablet

Gastric retention in unfed beagle dogs of a tablet/fiber coil device consisting of a non-disintegrating BaSo$_4$ tablet (0.64 cm diameter × 0.32 cm thick) with a single PE/nylon fiber retention arm (20 cm length × 0.24 cm diameter) attached to one face of the tablet. The PE/nylon fiber retention arm was "set" in the shape of a coil, and was folded into a #000 gelatin capsule. This device opened in the stomach to form a configuration consisting of a coil with attached tablet, with an overall diameter of ~4 cm.
GASTRIC RETENTION AT VARIOUS TIMES (HOURS) POST-DOSE

| DOG | 1 | 2 | 3 | 4 | 24 |
|---|---|---|---|---|---|
| A | I/I | O/I | O/I | O/I | O/I |
| C | O/I | O/I | O/I | O/I | O/I |
| D | O/I | O/I | O/I | O/I | O/I |

EXAMPLE 5

A tablet with an attached concentric coil was prepared. In this case, the coil did not consist of a fiber, but consisted of a nylon ribbon of dimensions 20 cm length × 0.5 cm diameter × 0.05 cm thickness. This ribbon was attached to the side of a non-disintegrating BaSO$_4$ tablet (0.64 cm diameter × 0.32 cm thick) by cyanoacrylate glue, coiled around the tablet edge, partially uncoiled to an overall diameter (tablet plus concentric coil) of ~4 cm, set by heating at 70° C. for 6 hours, recoiled, and placed in a #000 gelatin capsule, as in Example 4. The nylon ribbon retention arm on this device was significantly more flexible than the PE/nylon fiber retention arm of Example 4.

Tablet/ribbon coil devices prepared as described above were dosed to fasted beagle dogs who were fed their normal daily food ration at ~7 hours post-dose. Table V presents the duration of gastric retention of these devices in beagle dogs. Gastric retention of the devices was variable, with observed retention durations of 0, 4 and 24 hours in three dogs. Radiographs of devices in the small intestine indicated that the concentric nylon ribbon retention arm was deformed and followed the tablet in its transit down the small intestine. Thus attachment of a single flexible concentric nylon ribbon retention arm of the flexibility used herein is not sufficient to reproducibly hold a tablet in the stomach for ~24 hours.

TABLE V

Tablet with Concentric Ribbon Coil Retention Arm

Gastric retention in unfed beagle dogs of tablet/ribbon coil devices, consisting of a non-disintegrating BASO$_4$ tablet (0.64 cm diameter × 0.32 cm thickness) with a nylon ribbon retention arm (20 cm length × 0.5 cm diameter × 0.05 cm thickness) attached to the tablet edge. These devices opened in the stomach to form a configuration consisting of a tablet with a concentric coil, with an overall diameter of ~4 cm.
GASTRIC RETENTION AT VARIOUS TIMES (HOURS) POST-DOSE

| DOG | 1 | 2 | 3 | 4 | 5 | 6 | 24 |
|---|---|---|---|---|---|---|---|
| A | O/I | O/O | NM | NM | NM | NM | NM |
| C | I/I | I/I | O/I | O/I | O/I | O/I | O/I |
| D | I/I | I/I | I/I | I/I | O/O | O/O | O/O |

EXAMPLE 6

A device was prepared consisting of a tablet with four curved nylon ribbon retention arms attached to the tablet edge. A tightly fitting cylindrical polyvinylchloride sleeve was placed around the edge of a nondisintegrating radiopaque $BaSO_4$ tablet (0.64 cm diameter $\times$ 0.32 cm thickness). The dimensions of the tablet plus concentrically attached sleeve were 1.03 cm diameter $\times$ 0.32 cm thickness. One end of each of four nylon ribbons was glued to the outer edge of the sleeve with a cyanoacrylate glue, in a tangential fashion. The dimensions of each ribbon were 4 cm length $\times$ 0.4 cm width $\times$ 0.05 cm thickness. Note that, except for the length, these ribbons were approximately the same width and thickness as the nylon ribbon used in Example 5, and had the same degree of flexibility. The four ribbon retention arms (attached to the tablet) were coated with a small amount of cyanoacrylate glue, and were sprinkled with stainless steel powder, to make the ribbons radiopaque. The ribbon retention arms were coiled tightly around the sleeve edge, then were placed in an aluminum foil container which permitted the device to partially uncoil to an overall diameter of $\sim$3.5–4.0 cm (tablet plus sleeve plus inwardly curved ribbon retention arms). The partially uncoiled device was heated at 70° C. for 6 hours to permit the nylon ribbon retention arms to set in said configuration. Approximately one day prior to dosing, the tablet/sleeve/ribbon coil device was tightly recoiled and was placed in a #13 veterinary gelatin capsule.

This device was dosed (along with a radiopaque control tablet) to a fasted beagle dog, which was fed its normal daily food ration at $\sim$7 hours post-dose. Gastric retention was assessed by radiography at 6 and 24 hours. The tablet/sleeve/ribbon coil device was observed to be present in the stomach at 24 hours, while the control tablet had exited the stomach by 6 hours post-dose.

EXAMPLE 7

A preferred embodiment of the current invention is one in which the gastric retention device is retained in the stomach effectively indefinitely, and moves out of the stomach when the device changes shape, falls apart, degrades or dissolves. Thus the duration of retention can be dictated by the design of the degradation mechanism, minimizing the effects of patient-to-patient variability in gastric physiology. This example demonstrates an approach for achieving a device which performs this way. This device is similar to that described in Example 6, but incorporates a mechanism for disintegration.

A disintegrating device was prepared as follows. A radiopaque non-disintegrating $BaSO_4$ tablet (1.03 cm diameter $\times$ 0.32 cm thickness) was prepared. A cylindrical sleeve (1.03 cm inner diameter; 1.11 cm outer diameter) composed of 95% polyvinylacetate phthalate (PVAP) and 5% Hycar rubber particles to decrease brittleness was prepared. PVAP is an "enteric" material, i.e. one which retains its physical properties at low pH but softens and dissolves at neutral to high pH. The cylindrical PVAP sleeve was placed over the tablet and was firmly attached to the tablet with a cyanoacrylate glue. Four nylon ribbons (4 cm length $\times$ 0.4 cm width $\times$ 0.05 cm thickness) were attached with cyanoacrylate glue to the outer edge of the cylindrical PVAP sleeve in a tangential fashion. These nylon ribbon retention arms possessed approximately the same degree of flexibility as those in Examples 5 and 6. The four ribbons were coated with a small amount of glue, and were sprinkled with stainless steel powder to make the ribbons radiopaque. The ribbon retention arms were coiled tightly around the sleeve edge, then were placed in an aluminum foil container which permitted the device to partially uncoil to an overall diameter of $\sim$3.5–4.0 cm (tablet plus sleeve plus inwardly curved ribbon retention arms). The partially uncoiled device (in the foil container) was heated at 70° C. for 6 hours to permit the nylon ribbon retention arms to set in said configuration. Approximately one day prior to dosing, the tablet/sleeve/ribbon coil device was tightly recoiled, and was placed in a #13 veterinary gelatin capsule. Devices of this type opened to an overall diameter of $\sim$3.6 cm when removed from the capsule.

Other devices were prepared which were identical to those described above, except for the method of making the ribbon retention arms radiopaque. Rather than coating the entire ribbon with glue and stainless steel powder, only $\sim$1 cm of the outer tip of each ribbon was made radiopaque with glue and stainless steel powder. This was done to test the possibility that retention of devices in which the entire ribbon was covered with glue and steel powder might be due to ribbon stiffness imparted by the glue/powder, rather than by the intrinsic stiffness of the nylon ribbon retention arms themselves.

Devices of these types were dosed to fasted beagle dogs who were fed their normal daily food ration at $\sim$7 hours post-dose. Table VI presents the duration of gastric retention of these devices. In all cases, the tablet/ribbon coil devices were gastrically retained for at least 20 hours. When devices were observed in the small intestine or colon by radiography, it was clear that the nylon ribbon retention arms had either fallen off or were bent at the PVAP base and were in the process of falling off. By designing a device which is consistently retained until it falls apart after a predetermined period, two problems are avoided: (1) patient-to-patient variability in the ability of "housekeeper waves" to empty devices from the stomach, and (2) the potential for a patient to have numerous devices collect in the stomach or intestine.

The devices of this Example (and Example 6), which had 4 short ribbon retention arms arranged concentrically around the tablet edge, were effective gastric retention devices. On the other hand, the devices of Example 5, which had a single ribbon retention arm arranged concentrically around the tablet, exhibited variable gastric retention. In both cases, the devices opened to a diameter of $\sim$4 cm. Thus successful retention of these devices depended not only upon the size of the device, but also upon the configuration of the attached ribbon retention arms which formed the expanded coil.

TABLE VI

Tablet with Four Ribbon Retention Arms Forming Biodegradable Coil

Gastric retention in unfed beagle dogs of tablet/ ribbon coil device consisting of a non-disintegrating $BaSO_4$ tablet (1.03 cm diameter $\times$ 0.32 cm thickness), and a degradable PVAP sleeve to which four nylon ribbon retention arms were attached, as described in Example 7. The ribbon dimensions were 4 cm length $\times$ 0.4 cm width $\times$ 0.05 cm thickness. This device uncoiled in the stomach to form a configuration which had an overall TABLE VI-continued Tablet with Four Ribbon Retention Arms Forming Biodegradable Coil
diameter of ~3.6 cm. (A) With ribbons totally covered with glue and stainless steel powder to provide radiopacity; (B) with only ribbon tips covered with glue and stainless steel powder to provide radiopacity;

GASTRIC RETENTION AT VARIOUS TIMES (HOURS) POST-DOSE

| DEVICE | 1 | 3 | 4 | 5 | 6 | 20 | 24 |
|---|---|---|---|---|---|---|---|
| (A) | | | | | | | |
| Dog A | O/I | O/I | O/I | O/I | O/I | O/I | O/I |
| Dog C | O/I | O/I | O/I | O/I | O/I | O/I | O/I |
| Dog D | I/I | I/I | I/I | I/I | I/I | O/I | O/O |
| (B) | | | | | | | |
| Dog C | O/I | O/I | O/I | O/I | O/I | O/I | O/I |
| Dog D | I/I | I/I | I/I | I/I | I/I | O/I | O/I |

EXAMPLE 8

Controlled release tablets containing the antidiabetic drug glipizide were inserted into receptacles of radiopaque GI retention devices as described in Example 7. These devices were dosed to three fasted beagle dogs, which were subsequently fed at 12 hours post-dose. In a control experiment, the same dogs were dosed with identical controlled release glipizide tablets without GI retention devices. Blood was drawn at various times post-dose, and glipizide plasma levels were determined, using an HPLC assay. In the case of dosing without a GI retention device, the average $T_{max}$ (time at which peak plasma concentration was observed) was 2.7 hours and the average AUC (area under the plasma concentration vs. time curve) was 35 microgm-hr/ml. In the case of dosing with a GI retention device, an approximately constant glipizide plasma level was observed which extended from 3 hours to 12 hours post-dose, and an average AUC of 64 microgm-hr/ml was observed. Concurrent x-ray measurements indicated that the glipizide-releasing GI retention devices were located in the stomach for at least 8 hours. This example clearly demonstrates that a GI retention system of the current invention can be used to improve the performance of a controlled release drug delivery system, by assuring that the drug is delivered in an absorbable form to the upper portion of the small intestine, where absorption is generally most efficient.

What is claimed:

1. A modular system for use in an oral drug delivery system in a mammal, having delayed gastrointestinal transit, which releases a drug or drugs in a controlled manner in said gastrointestinal tract and exits said gastrointestinal tract after said drug or drugs have been substantially released, said modular system comprising a receptacle means for receiving and containing an orally administrable controlled release device and one or more fibers or ribbons attached to said receptacle means, said fibers or ribbons, collectively:
    (a) being restrained in a contracted configuration at the time of dosing, and
    (b) uncoiling, unrolling, or unfolding after entry into the stomach, into a configuration having a circular or roughly circular cross-section having a diameter of at least about three centimeters,
   said modular system capable of softening, disintegrating, dissolving or degrading in the biological environment of the stomach in order to permit the exit of the modular system therefrom.

2. A modular system according to claim 1 wherein said receptacle means is a collar which fits about and holds a controlled release device.

3. A modular system according to claim 1 wherein said receptacle means comprises an opened wall member with an internal space for receiving and holding said device.

4. A modular system according to claim 3 wherein said receptacle means is capped for closing the receptacle means holding the device, said wall and/or said capped member having a passageway to permit passage of environmental fluid into the receptacle means and passage of drug therefrom to the environment.

5. A modular system according to claim 1 wherein one end of said ribbons or fibers are attached to said receptacle.

6. A modular system according to claim 1 wherein two or more ribbons or fibers of substantially equal size are attached to the receptacle.

7. A modular system according to claim 6 wherein the ribbons or fibers are symmetrically spaced about the receptacle.

8. A modular system according to claim 7 having, in the expanded state, a size of from about 2.5 to 6.0 cm in its largest dimension.

* * * * *